US012780757B2

(12) United States Patent
Zong et al.

(10) Patent No.: US 12,780,757 B2
(45) Date of Patent: Nov. 3, 2026

(54) CATALYST MIXING DEVICE

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Hongyuan Zong, Shanghai (CN); Xiaohong Li, Shanghai (CN); Guozhen Qi, Shanghai (CN); Yongming Jin, Shanghai (CN); Pan Gao, Shanghai (CN); Yanxue Wang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 866 days.

(21) Appl. No.: 18/245,247

(22) PCT Filed: Sep. 15, 2021

(86) PCT No.: PCT/CN2021/118392

§ 371 (c)(1),
(2) Date: Mar. 14, 2023

(87) PCT Pub. No.: WO2022/057805

PCT Pub. Date: Mar. 24, 2022

(65) Prior Publication Data

US 2023/0364572 A1 Nov. 16, 2023

(30) Foreign Application Priority Data

Sep. 15, 2020 (CN) ........................ 202010968050.4

(51) Int. Cl.
*C07C 1/22* (2006.01)
*B01J 8/00* (2006.01)
(Continued)

(52) U.S. Cl.
CPC ................. *C07C 1/22* (2013.01); *B01J 8/001* (2013.01); *B01J 8/0015* (2013.01); *B01J 8/007* (2013.01);
(Continued)

(58) Field of Classification Search
CPC . B01J 8/001; B01J 8/0015; B01J 8/005; B01J 8/007; B01J 8/008; B01J 8/08;
(Continued)

(56) References Cited

U.S. PATENT DOCUMENTS 6,166,282 A 12/2000 Miller
6,736,960 B1 * 5/2004 Chen ........................ B01J 19/26 239/398
(Continued)

FOREIGN PATENT DOCUMENTS

CN 101698629 A 4/2010
CN 102276398 A 12/2011
(Continued)

*Primary Examiner* — Natasha E Young
(74) *Attorney, Agent, or Firm* — NKL Law; Allen Xue

(57) ABSTRACT

A mixing device for mixing at least two particulate materials has a first riser used for loading first particles and a second riser surrounding and being coaxial with the riser and used for loading second particles. The upper part of the first riser extending beyond the top of the second riser. At least a part of the upper part of the first riser and at least a part of the upper part of the second riser being located inside a mixing zone container, such that the first and second particles are delivered to the inside of the mixing zone container by means of the first and second risers respectively and mixed.

12 Claims, 7 Drawing Sheets

(51) Int. Cl.

| | |
|---|---|
| ***B01J 8/08*** | (2006.01) |
| ***B01J 8/18*** | (2006.01) |
| ***B01J 8/26*** | (2006.01) |
| ***B01J 29/85*** | (2006.01) |
| ***B01J 29/90*** | (2006.01) |
| ***B01J 38/02*** | (2006.01) |
| ***C07C 11/04*** | (2006.01) |
| ***C07C 11/06*** | (2006.01) |

(52) U.S. Cl.
CPC ............... *B01J 8/008* (2013.01); *B01J 8/085* (2013.01); *B01J 8/087* (2013.01); *B01J 8/1827* (2013.01); *B01J 8/1863* (2013.01); *B01J 8/26* (2013.01); *B01J 29/85* (2013.01); *B01J 29/90* (2013.01); *B01J 38/02* (2013.01); *C07C 11/04* (2013.01); *C07C 11/06* (2013.01); *B01J 2208/00017* (2013.01); *B01J 2208/00539* (2013.01); *C07C 2529/85* (2013.01)

(58) Field of Classification Search
CPC ..... B01J 8/085; B01J 8/087; B01J 8/18; B01J 8/1809; B01J 8/1818; B01J 8/1827; B01J 8/1845; B01J 8/1863; B01J 8/24; B01J 8/26; B01J 8/38; B01J 8/384; B01J 8/388; B01J 8/44; B01J 29/00; B01J 29/82; B01J 29/84; B01J 29/85; B01J 29/90; B01J 38/00; B01J 38/02; B01J 2208/00; B01J 2208/00008; B01J 2208/00017; B01J 2208/00106; B01J 2208/00168; B01J 2208/00176; B01J 2208/00539; C07C 1/00; C07C 1/20; C07C 1/22; C07C 11/00; C07C 11/02; C07C 11/04; C07C 11/06; C07C 2529/00; C07C 2529/82; C07C 2529/84; C07C 2529/85; C10G 11/00; C10G 11/14; C10G 11/18; C10G 2400/00; C10G 2400/20
See application file for complete search history.

(56) References Cited

U.S. PATENT DOCUMENTS

| | | | | |
|---|---|---|---|---|
| 2006/0025646 | A1 | 2/2006 | Fung et al. | |
| 2010/0331596 | A1 | 12/2010 | Xie et al. | |
| 2011/0306811 | A1 | 12/2011 | Qi et al. | |
| 2012/0271088 | A1 | 10/2012 | Wei | |
| 2013/0150233 | A1 | 6/2013 | Wolschlag et al. | |
| 2013/0252803 | A1 | 9/2013 | Johnson et al. | |
| 2014/0275675 | A1 | 9/2014 | Eng | |
| 2016/0304413 | A1 | 10/2016 | Liu et al. | |
| 2017/0305815 | A1* | 10/2017 | Cui | B01J 29/06 |
| 2023/0348340 | A1* | 11/2023 | Zong | B01J 8/087 |

FOREIGN PATENT DOCUMENTS

| | | | |
|---|---|---|---|
| CN | 102372538 | A | 3/2012 |
| CN | 102464534 | B | 11/2014 |
| CN | 107540497 | A | 1/2018 |
| CN | 108079912 | A | 5/2018 |
| EP | 1140743 | B1 | 10/2005 |
| EP | 2334760 | B1 | 10/2014 |
| WO | 2016109367 | A1 | 7/2016 |
| WO | 2021003083 | A1 | 1/2021 |

* cited by examiner

CATALYST MIXING DEVICE

This application is a national stage application of International Patent Application No. PCT/CN2021/118392, now WO 2022/057805, filed on Sep. 15, 2021, that claims foreign priority to Chinese Patient Application No. 202010968050.4, filed on Sep. 15, 2020, the contents of each of which are incorporated herein by reference in their entirety.

TECHNICAL FIELD

The present invention relates to a device for mixing at least two particulate catalysts, and in particular, the device is particularly suitable for use in a reaction system for producing ethylene-propylene.

BACKGROUND

Lower olefins, namely ethylene and propylene, are two important basic chemical feedstocks, and the demand of the lower olefins is increasing continuously. In recent years, the process of Methanol to Olefins (MTO) has been greatly developed, and three technologies have been industrially applied, and many related patents exist.

CN102464534B and CN102372538A disclose zoned processes of MTOs, wherein methanol enters a lower premixing zone or a catalyst mixing tube and an upper main reaction zone respectively for reaction.

In the process disclosed in CN102276398A, liquid methanol enters an initial contacting zone to exchange heat with a spent catalyst, and then goes upward to enter a main reaction zone to react to generate ethylene and propylene.

According to the scheme above, as the reaction conditions in the premixing area, the catalyst mixing tube and the initial contacting area are not suitable for methanol conversion, the carbon-based loss of methanol is caused, and the selectivity to the both olefins is low. In particular, in MTO processes, particulate catalysts are involved in deactivation (especially, for example, coking) and regeneration, while a certain extent of coking of the catalyst may be beneficial to the reaction. Thus, in an MTO process, it is desirable to rapidly mix a regenerated catalyst with a coked-deactivated catalyst in a certain ratio.

SUMMARY OF THE INVENTION

One of the technical problems to be solved by the present invention is to overcome the defect that a plurality of particulate catalysts are not easy to be quickly and uniformly mixed in the prior art, and is particularly suitable for an ethylene-propylene production process of an MTO process.

Based on research and improvement to the MTO process, the present invention provides a mixing device for mixing at least two particulate catalysts, comprising a riser for loading a first particulate catalyst and an outer casing vessel surrounding and being coaxial with the riser for loading a second particulate catalyst, the first and second particulate catalysts being different in structure and/or composition, and at least a part of the upper portion of the riser and at least a part of the upper portion of the outer casing vessel both being located inside a mixing zone vessel; wherein:

the bottom of the riser is provided with a riser feed inlet for a first lifting medium, which is used for delivering upwards the first particulate catalyst loaded in the riser; the top of the riser has a riser outlet structural member for allowing the upward-delivered first particulate catalyst to be fed into the interior of the mixing zone vessel via the riser outlet structural member;

the bottom of the outer casing vessel is provided with a second lifting medium feed inlet, which is used for delivering upwards the second particulate catalyst loaded in the outer casing vessel; the top of the outer casing vessel is provided with an outer casing vessel outlet structural member which is used for allowing the second particulate catalyst delivered upwards to be fed into the interior of the mixing zone vessel through the outer casing vessel outlet structural member and be mixed with the first particulate catalyst to obtain a mixed catalyst.

In a preferred embodiment, the first and second particulate catalysts are distributed such that the Peclet number of the mixed catalyst is less than 5, and the mean square error, σ, of the first particulate catalyst fraction is less than 3.0; or the Peclet number of the mixed catalyst is less than 1, and the mean square error, σ, of the first particulate catalyst fraction is less than 1.0.

In a preferred embodiment, the ratio by weight of the flow rates entering the mixing zone vessel, Rw, of the first particulate catalyst to the second particulate catalyst is $0.01<Rw\leq 0.5$, preferably $0.02<Rw\leq 0.2$.

In a preferred embodiment, the mixing device of the present invention may be used in a process for producing ethylene-propylene, wherein the outer casing vessel is a fast bed reactor; the mixing zone vessel is preferably a fast bed settler; and/or the riser outlet structural member and the fast bed outlet structural member are each preferably a fast separator.

In a preferred embodiment, the riser is externally provided with a heat-exchanging coiler or jacket, for removing or supplementing heat from/to the riser and/or outer casing vessel.

The present invention also provides a reaction system for producing ethylene-propylene, comprising: a fast bed reactor, a fast bed settler and a riser which are coaxially arranged; wherein the riser is located, in the radial direction, within the fast bed reactor; the bottom of the riser is provided with a riser feed inlet for a first lifting medium; the top outlet of the riser is connected with a riser outlet structural member through which the regenerated first particulate catalyst obtained by a regeneration treatment and optional other treatment is delivered into the fast bed settler;

the fast bed reactor is used for allowing that contact and reaction of the feedstocks with the catalyst to produce ethylene-propylene is mainly carried out therein, during which reaction the catalyst is at least partially deactivated; the top of the fast bed reactor is connected with a fast bed outlet structural member, a second particulate catalyst obtained from the partial deactivation is delivered into the fast bed settler and is mixed with the regenerated first particulate catalyst to obtain a mixed catalyst;

the riser outlet structural member and the fast bed outlet structural member are both located inside the fast bed settler, and the riser outlet structural member is located above the fast bed outlet structural member;

wherein the riser outlet structural member and the fast bed outlet structural member are each preferably a fast separator.

The present invention also provides a mixing device for mixing at least two particulate materials, comprising a riser for loading a first particle and an outer casing vessel surrounding and being coaxial with the riser for loading a second particle, the upper portion of the first riser extending beyond the top of the second riser, and at least a part of the upper portion of the first riser and at least a part of the second riser both being located inside a mixing zone vessel, such that the first and second particles are delivered through the first and second risers, respectively, to the interior of the mixing zone vessel and mixed.

Accordingly, the present invention also provides an exemplary process for producing ethylene-propylene, comprising:

a) feeding a methanol feedstock into a fast bed reactor to be contacted and reacted with a catalyst to obtain a reaction product I, and feeding a second particulate catalyst obtained from partial deactivation through a fast separator of the fast bed into a fast bed settler;

b) feeding a part of the mixed catalyst from the fast bed settler into a stripper, and returning a part of the mixed catalyst to the fast bed reactor, and feeding another part of the mixed catalyst into an outside heat-exchanger to be contacted with a heat-removing medium for cooling followed by being returned to the fast bed reactor;

c) feeding a light hydrocarbon feedstock and an oxygenate feedstock into the outside riser reactor to be contacted with the catalyst, for reaction during the upward delivering thereof, and being fed into the riser settler, to obtain a reaction product II and a first particulate catalyst, wherein the oxygenate feedstock contains water and an oxygenate;

d) feeding a part of the first particulate catalyst from the riser settler into the stripper, and another part of the first particulate catalyst into the riser; wherein the first particulate catalyst fed into the riser enters the fast bed settler through the riser fast separator by the lifting of a first lifting medium;

e) feeding the catalyst from the stripper, after being stripped by a stripping medium, into a regenerator to be contacted with a regenerating medium to burn coke on the catalyst to obtain a regenerated catalyst and flue gas;

f) degassing the regenerated catalyst and then feeding the degassed regenerated catalyst into the outside riser reactor; and feeding the reaction product I and the reaction product II together into a separation unit to obtain a product rich in ethylene and propylene, $C_4$-$C_6$ non-aromatic hydrocarbon mixture and an aqueous phase, wherein a part or all of the aqueous phase is used as the oxygenate feedstock.

In the present invention, the reaction products referred to in the various embodiments, including, for example, the reaction product I, the reaction product II, and additional reaction product, etc., as indicated, each represent a material obtained by a reaction intended to provide products of ethylene and propylene, and capable of providing products rich in ethylene and propylene by means of separation units known in the art, but the specific composition thereof may differ somewhat in the various embodiments due to variations in the starting materials, reaction conditions, etc., within the scope of the present invention.

In the technical solutions for producing ethylene-propylene by catalytic conversion of methanol, $C_4$-$C_6$ non-aromatic hydrocarbon and an aqueous solution of oxygenate are contacted and reacted with a regenerated catalyst in an outside riser reactor, and are converted into ethylene and propylene at high selectivity under the conditions of high temperature and high linear velocity, so that the generation of heavy hydrocarbon and phenol compounds is avoided.

Meanwhile, the regenerated catalyst obtained is fully mixed with the second particulate catalyst obtained by partial deactivation in a fast bed settler through a special fast separator structure and then is fed into the reaction zone of the fast bed reactor to participate in the MTO reaction, so that high selectivity to ethylene and propylene can be obtained.

According to an embodiment of the invention, using the SAPO-34 catalyst, the total yield, calculated as carbon, of the ethylene and propylene can reach 90.4 wt %, representing a desirable technical effect.

DESCRIPTION OF SOME REFERENCE SIGNS

Figure 1:
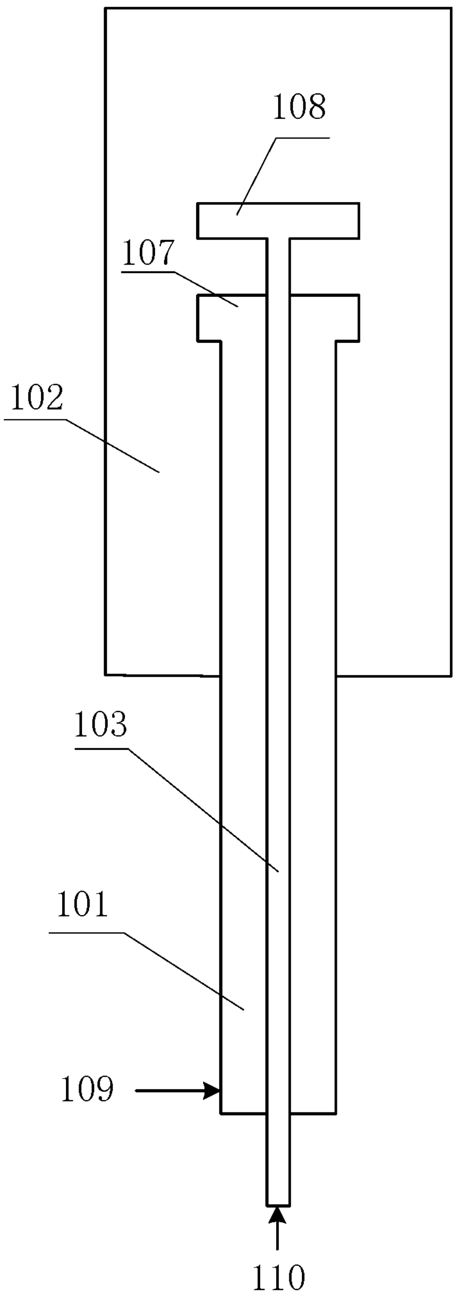
FIG. 1 shows a schematic figure of a mixing device according to one embodiment of the present invention.

101 denotes an outer casing vessel; 102 denotes a mixing zone vessel; 103 denotes a riser; 107 denotes an outer casing vessel outlet structural member; 108 denotes a riser outlet structural member; 109 denotes a second lifting medium feed inlet; 110 denotes a riser feed inlet for a first lifting medium;

201 denotes a fast bed reactor; 202 denotes a fast bed settler; 203 denotes a riser; 204 denotes a lifting zone of the fast bed reactor; 205 denotes an outside riser reactor; 206 denotes a riser settler; 207 denotes a fast bed fast separator; 208 denotes a riser fast separator; 209 denotes a feed inlet for methanol; 210 denotes an inlet for a first lift medium; 211 denotes an inlet for a refreshed feedstock; 212 denotes a product outlet;

32 denotes the top of the lower branch pipe of the fast bed fast separator; 33 denotes a diffuser plate; 34 denotes a diffuser cone;

38 denotes a lower branch pipe of the fast bed fast separator (fast bed fast separator lower branch pipe); 39 denotes a lower branch pipe of the riser fast separator (riser fast separator lower branch pipe);

40 denotes a horizontal pipe of the fast separator; 41 denotes a horizontal pipe of the fast separator of the riser.

EMBODIMENTS

The present invention will be illustrated in detail in the embodiments referring to the drawings. It should be understood that the detailed description and specific Examples, while indicating the preferred embodiments of the invention, are given by way of illustration and explanation only, without limiting the present invention.

In the description of the present invention, it is to be understood that the orientation or position relationship indicated by terms "transverse" direction, "radial" direction, "circumferential" direction, "inner", "outer" and the like refer to the orientation or position relationship in the drawings, which are provided for convenience of easy and simple description, but not to indicate or imply that a device or part so referred to must have a particular orientation, be constructed and operated in a particular orientation, and thus, are not to be considered as limitation to the present invention.

In the present invention, a same reference sign generally denotes the same/corresponding object.

In the present invention, the pressure is gauge pressure unless otherwise specified.

As showed in FIG. 1, the present invention provides a mixing device for mixing at least two particulate catalysts, comprising a riser (103) for loading a first particulate catalyst and an outer casing vessel (101) surrounding and being coaxial with the riser for loading a second particulate catalyst, the first and second particulate catalysts being different in structure and/or composition, and at least a part of the upper portion of the riser (103) and at least a part of the upper portion of the outer casing vessel (101) both being located inside a mixing zone vessel (102);

wherein the bottom of the riser (103) is provided with a riser feed inlet (110) for a first lifting medium, which is used for delivering upwards the first particulate catalyst loaded in the riser (103); the top of the riser (103) has a riser outlet structural member (108) for allowing the upward-delivered first particulate catalyst to be fed into the interior of the mixing zone vessel (102) via the riser outlet structural member (108);

The bottom of the outer casing vessel (101) is provided with a feed inlet (109) for a second lifting medium, which is used for delivering upwards the second particulate catalyst loaded in the outer casing vessel (101); the top of the outer casing vessel (101) has an outer casing vessel outlet structural member (107) for allowing the upward-delivered second particulate catalyst to be fed into the interior of the mixing zone vessel (102) via the outer casing vessel outlet structural member (107), and to be mixed with the first particulate catalyst, so as to obtain a mixed catalyst.

Figure 2:
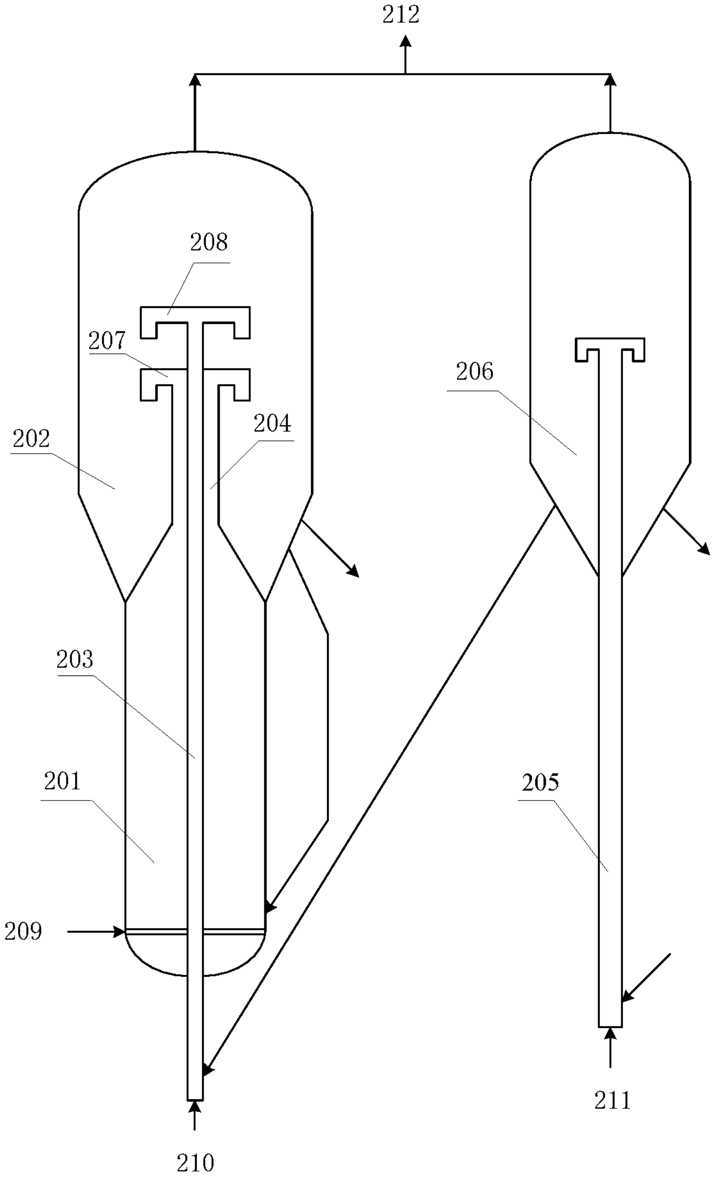
FIG. 2 shows a schematic figure of a reaction system for producing ethylene-propylene according to one embodiment of the present invention.

As shown in FIG. 2, the present invention provides a reaction system for producing ethylene-propylene, which uses a mixing device as shown in FIG. 1 as a main part of a reaction functional zone, and an outside lifting/regeneration zone is connected to the outside of the reaction functional zone. The reaction system thus comprises:

a reaction function zone, comprising: a fast bed reactor 201 having a lifting zone 204 with decreased radius in its upper portion (corresponding to the outer casing vessel 101 shown in FIG. 1), a fast bed settler 202 (corresponding to the mixing zone vessel 102 shown in FIG. 1), a riser 203 (corresponding to the riser 103 shown in FIG. 1), a methanol feed inlet 209 (corresponding to the second lifting medium 109 shown in FIG. 1), optionally an outside heat-exchanger (located outside the mixing device and not shown in the figure); and an outside lifting/regeneration zone comprising: an outside riser reactor 205, a riser settler 206, optionally a stripper (not shown in the figure), optionally a regenerator (not shown in the figure).

In one embodiment, the riser 203 and the fast bed reactor 201 are coaxial with the fast bed settler 202, the fast bed reactor 201 surrounding the riser 203; the outlet of the riser 203 is connected with a riser outlet structural member 208 (such as a fast separator), and the top of the fast bed reactor 201 is connected with a fast bed outlet structural member 207 (such as a fast separator); the riser fast separator 208 and the fast bed fast separator 207 are both located within the fast bed settler 202. In one embodiment, the riser fast separator 208 is located above the fast bed fast separator 207. In one embodiment, the riser outlet structural member 208 (see FIGS. 6 and 7) is located inside the fast bed fast separator 207, the outside riser reactor 205 is coaxial with the riser settler 206, and the upper portion and the outlet of the outside riser reactor 205 are located inside the riser settler 206.

Accordingly, in the present invention, in view of the correspondence in FIGS. 1 and 2 described above, the various embodiments and technical features discussed with respect to the outer casing vessel 101 and the corresponding fast bed reactor 201, respectively, are all applicable interchangeably with each other, unless the object of the present invention is obviously departed; and so does the mixing zone vessel 102 with the corresponding fast bed settler 202, and the riser 103 with the corresponding riser 203. In addition, other devices/components not specifically indicated but corresponding to the reference signs in FIGS. 1 and 2, such as devices/components represented by 107, 108, 109, and 110, have such an interchangeable relationship with devices/components represented by 207, 208, 209, and 210.

Still further, even if not specifically indicated or labeled in the drawings, it will be readily understood by those skilled in the art that the various devices/components discussed, referred to in the present invention and/or labeled in the drawings are generally applicable to the device for mixing at least two particulate catalysts shown in FIG. 1 and the reaction system for producing ethylene-propylene shown in FIG. 2, respectively, and also to the other illustrated, preferred or specifically mentioned embodiments of the present invention, unless the purpose of the present invention or the specific purpose of a corresponding embodiment is not satisfied.

Figure 3:
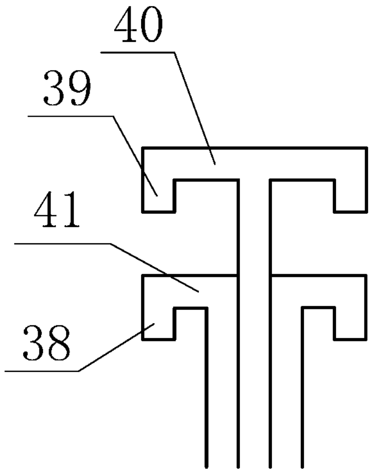
FIGS. 3-5 show schematic figures for the detailed connection of the riser outlet structural member (fast separator) with the outer casing vessel outlet structural member (fast separator) according to an embodiment of the present invention.

For example, the structure of the riser fast separator 208 discussed herein and illustrated in FIG. 3 is a specific example of the reaction system for producing ethylene-propylene shown in FIG. 2, but is also suitable for the mixing device for mixing at least two particulate catalysts shown in FIG. 1, as well as other embodiments encompassed by the present invention, unless the purpose of the present invention or the specific purpose of a corresponding embodiment is not satisfied. For another example, the methanol feed inlet 209 shown in FIG. 2 corresponds to the second lifting medium feed inlet 109 shown in FIG. 1, wherein the methanol feed is capable of acting as a lifting medium in the reaction system relative to the catalyst with which it is in contact.

In one embodiment, the mixed catalyst outlet of the riser settler 206 is communicated with the feed inlet of the riser 203 and is communicated with the feed inlet of the stripper, the mixed catalyst outlet of the fast bed settler 202 is communicated with the feed inlet of the stripper and is communicated with the feed inlet of the outside heat-exchanger, the solid outlet of the stripper is communicated with the solid feed inlet of the regenerator, and the outlet of the heat-removed product of the outside heat-exchanger is communicated with the upper opening of the fast bed settler 202.

In one embodiment, the interior of the mixing zone vessel 202 is provided with an annular distributor surrounding and being coaxial with the upper portion of the outer casing vessel 201 for delivering upward a fluidizing gas (e.g., steam) into the interior of the mixing zone vessel 202 to act on the first and second particulate catalysts.

In the system of the invention, the aqueous solution of the oxygenate is contacted and reacted with the regenerated catalyst in the outside riser reactor 205, and is converted into lower hydrocarbons under the conditions of high temperature and high linear velocity, thereby avoiding generation of heavy hydrocarbons and phenol compounds. Meanwhile, the regenerated first catalyst obtained is delivered upward and fully mixed with the second particulate catalyst obtained by partial deactivation, and then is fed into the reaction zone of the fast bed reactor to be contacted and reacted with methanol, so that high selectivity to ethylene and propylene can be obtained.

In the present invention, cyclones, or any other device capable of performing a similar function (in particular, such as the separation of catalyst from product), may be provided in both the fast bed settler 202 and riser settler 206.

It is clearly understood by those skilled in the art that the mixing device of the present invention as shown in FIG. 1 can be used in a variety of applications involving the mixing of at least two particulate catalysts, in addition to the ethylene-propylene reaction system shown in FIG. 2, including but not limited to: mixing a fresh catalyst supplemented to a reaction system with the existing catalyst; feeding at least two catalysts due to instant operations such as mixing, compounding, blending and the like required by a reaction; returning the continuously regenerated catalyst during a reaction; and mixing catalysts having different activities.

In addition, it will be understood by those skilled in the art that the present invention also provides more broadly a mixing device for mixing at least two particulate materials, comprising a riser for loading a first particle and an outer casing vessel surrounding and being coaxial with the riser for loading a second particle, the upper portion of the first riser extending beyond the top of the second riser, and at least a portion of the upper portion of the first riser and at least a portion of the second riser both being located inside an upper vessel, such that the first and second particles are delivered through the first and second risers, respectively, to the interior of the upper vessel and mixed.

Referring to the illustrated embodiments of FIGS. 2 and 3, according to one embodiment of the present invention, the riser fast separators 208 is of a branch pipe structure, preferably lower branch pipes 39, and preferably the lower branch pipes 39 are uniformly distributed.

According to an embodiment of the present invention, the fast bed fast separator 207 is of a branch pipe structure, preferably lower branch pipes 38, and preferably the lower branch pipes 38 are uniformly distributed.

According to an embodiment of the invention, the riser fast separator lower branch pipe and the fast bed fast separator lower branch pipe 38 are distributed crosswise.

According to an embodiment of the present invention, the number, n, of the riser fast separator lower branch pipes 39 of the riser fast separator 208 is 2 to 8; and the included angle, β, between adjacent riser fast separator lower branch pipes 39 equals to 45-180 degrees. This embodiment is shown, for example, in FIG. 4.

According to an embodiment of the present invention, the number, m, of the fast bed fast separator lower branch pipes 38 of the fast bed fast separator 207 is 2 to 8; and the included angle, α, between adjacent fast bed fast separator lower branch pipes 38 equals to 45-180 degrees. This embodiment is shown, for example, in FIGS. 4 and 5.

According to an embodiment of the present invention, the distance from the center point of the fast bed fast separator 207 to the center point of the fast bed fast separator lower branch pipe 38 is less than or equal to the distance from the center point of the riser fast separator 208 to the riser fast separator lower branch pipe 39. More preferably, the ratio between the distance from the center point of the fast bed fast separator 207 to the center point of the fast bed fast separator lower branch pipe 38 and the distance from the center point of the riser fast separator 208 to the riser fast separator lower branch pipe 39 is 0.3-1:1.

Figure 4:
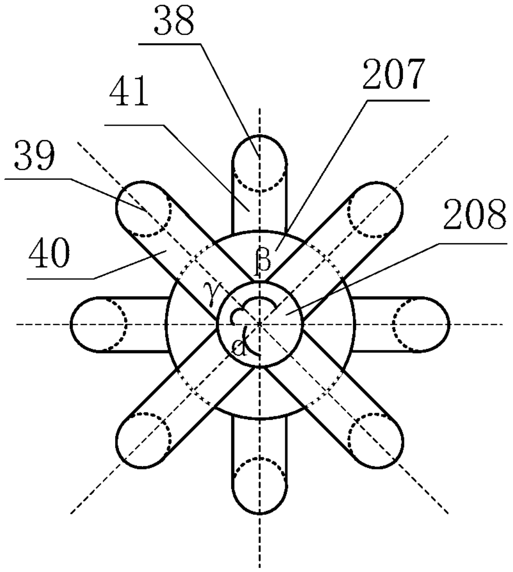
Figure 5:
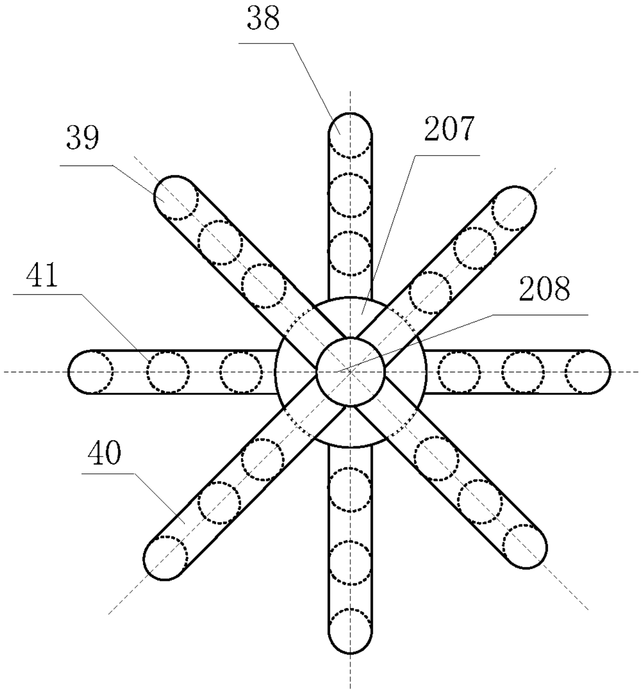

According to an embodiment of the invention, the upper portion of the riser 203 extends beyond the top of the lifting zone 204 of the fast bed reactor, so that the riser outlet structural member 208 is located above the fast bed outlet structural member 207. Such embodiments may be referred to as "above-below arrangement" in the present invention, which are illustrated, for example, in FIGS. 2 and 3, and the corresponding structure of FIG. 1. FIGS. 4 and 5 are specific illustrations of the outlet structural member 208 and the fast bed outlet structural member 207 that may be used in this above-below arrangement.

According to an embodiment of the present invention, the riser outlet structural member 208 is located inside the fast bed outlet structural member 207, such that the first particulate catalyst is premixed with the second particulate catalyst inside the fast bed outlet structural member 207. Such embodiments may be referred to as "inside arrangement" in the present invention, which are illustrated, for example, in FIGS. 6-8.

Similar to the previous discussion about the correspondence of the present invention, in the present invention, the mutual positional arrangement between the riser outlet structural member and the outer casing vessel outlet structural member (fast bed outlet structural member) is not limited to the discussion in each embodiment or the illustration in the corresponding figure(s), while the positional arrangement of the "above-below arrangement" or the "inside arrangement" may be independently selected as described above, unless the purpose of the present invention or the specific purpose of a corresponding embodiment is not satisfied.

Figure 6:
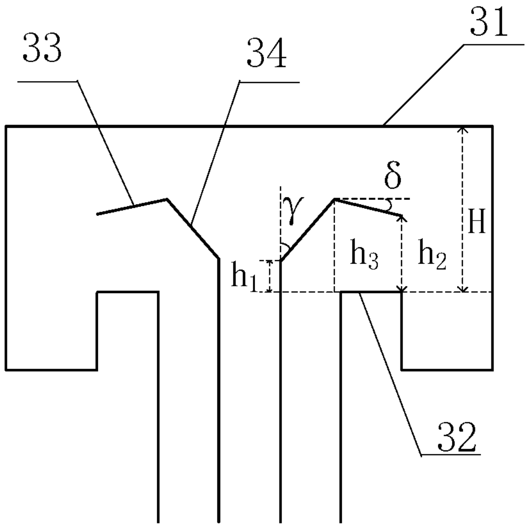
FIGS. 6 and 7 show schematic figures for the specific connection of the riser outlet structural members.

Referring to FIG. 6, according to an embodiment of the present invention, the riser outlet structural member 208 is a flow guiding structure, which is composed of an assembly of a diffusion cone 34 and a diffusion plate 33, the outlet of the riser 203 is connected to the diffusion cone 34, and the diffusion cone 34 is connected to the diffusion plate 33; the distance between the outlet of the riser 203 and the top 32 of the lower branch pipe of the fast bed fast separator is h1, the distance from the connection point of the diffusion cone 34 and the diffusion plate 33 to the top 32 of the lower branch of the fast bed fast separator is h3, the distance between the edge point of the diffusion plate 33 and the top 32 of the lower branch of the fast bed fast separator is h2, and the distance between the top 31 of the fast bed fast separator and the top 32 of the lower branch of the fast bed fast separator is H; the included angle between the diffusion cone 34 and the vertical direction is γ, and the included angle between the diffusion plate 33 and the horizontal direction is δ; the ratio of h1 to H is (0.05-0.3):1, the ratio of h2 to H is (0.2-0.5):1, and the ratio of h3 to H is (0.4-0.6):1; h3 is greater than h2; γ is 10-60 degrees, and δ is 30-80 degrees.

Figure 7:
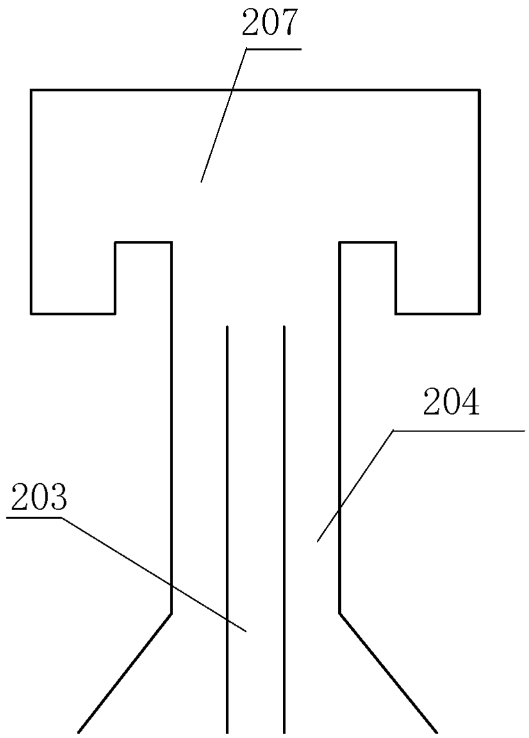

Referring to FIG. 7, according to an embodiment of the invention, the riser outlet structural member 208 adopts the upper portion of the riser 203 directly as a flow guiding member.

Figure 8:
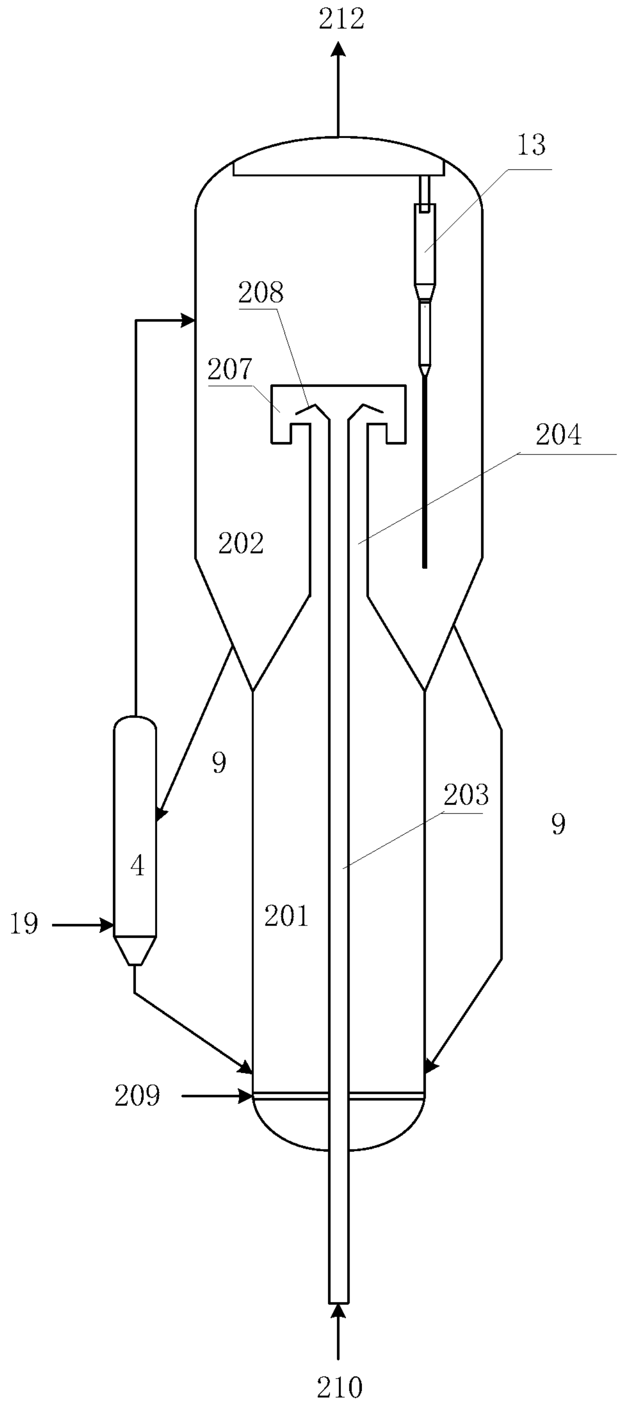
FIG. 8 shows a schematic figure of a mixing device according to one embodiment of the present invention.

Accordingly, referring to FIG. 8, which represents a variation of the mixing device of the present invention as showed in FIG. 1, which utilizes, for example, the riser outlet structural member 208 and the fast bed outlet structural member 207 in an "inside arrangement" as showed in FIG. 6, and is particularly useful in the system for producing ethylene-propylene as showed in FIG. 2, and particularly as the reaction functional zone of the system. According to this embodiment, the mixing device illustratively comprises an outside heat-exchanger 4 and a cyclone 13.

By using the system of the present invention, the yield of propylene-ethylene is high.

Figure 9:
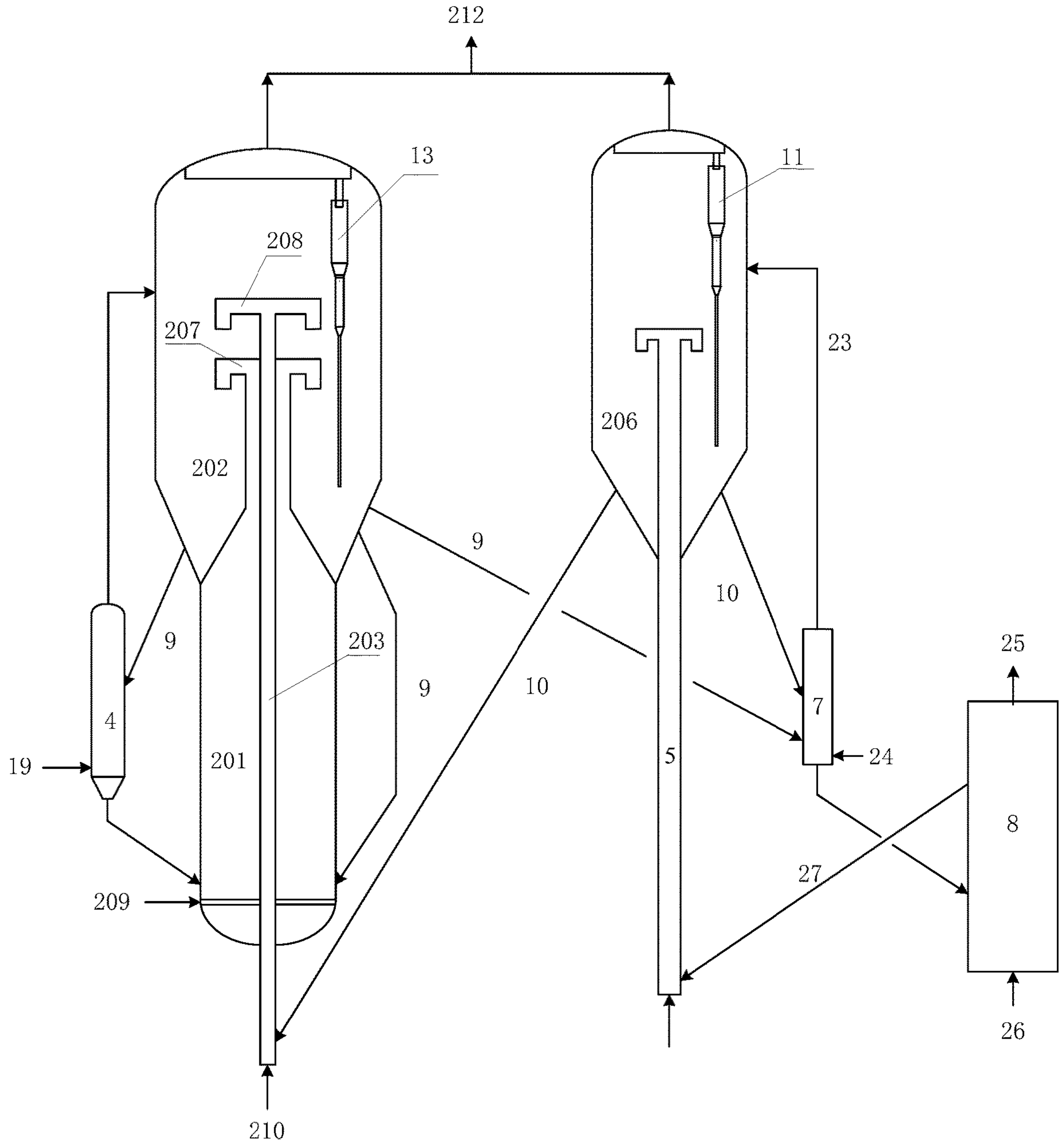
FIG. 9 shows a schematic figure of a reaction system for producing ethylene-propylene according to one embodiment of the present invention.

Referring to FIG. 9, it is a preferred embodiment of the reaction system of the present invention as shown in FIG. 2, comprising an outside heat-exchanger 4, a stripper 7 and a regenerator 8. Referring to FIG. 9 in combination with FIG. 2, according to an embodiment of the present invention, the present invention provides a process for producing ethylene-propylene, the process being carried out in a reaction system according to the present invention, the process comprising:

A) feeding a methanol feedstock into the reaction section of a fast bed reactor 201 through a methanol feed inlet 209 to be contacted and reacted with a catalyst to obtain a reaction product I (stream 22), from which a second particulate catalyst obtained from partial deactivation is delivered upward through the upper lifting zone 204 and is fed into a fast bed settler 202 through a fast bed fast separator 207;

b) feeding a part of the mixed catalyst (stream 9) from the fast bed settler 202 into a stripper, and returning a part of the mixed catalyst to the reaction section of the fast bed reactor 201, and feeding another part of the mixed catalyst into an outside heat-exchanger 4 to be contacted with a heat-removing medium 19 for cooling followed by being returned to the reaction section of the fast bed reactor 201;

c) feeding a light hydrocarbon feedstock and an oxygenate feedstock into the outside riser reactor 205 through the refreshed feedstock inlet 211 to be contacted with the regenerated catalyst, for reaction during the upward delivering thereof, and being fed into the riser settler 206, to obtain a reaction product II (stream 21) and a first particulate catalyst (stream 10), wherein the oxygenate feedstock contains water and an oxygenate;

d) feeding a part of the first particulate catalyst from the riser settler 206 into the stripper, and another part of the first particulate catalyst into the riser 203; wherein the first particulate catalyst fed into the riser 203 enters the fast bed settler 202 through the riser fast separator 208 by the lifting of a first lifting medium;

e) feeding the catalyst from the stripper, after being stripped by a stripping medium 24, into a regenerator to be contacted with a regenerating medium 26 to burn coke on the catalyst to obtain a regenerated catalyst and flue gas 25;

f) optionally, degassing the regenerated catalyst and then feeding the degassed regenerated catalyst (stream 27) into the outside riser reactor 205; and feeding the reaction product I and the reaction product II together via the product outlet 212 into a separation unit to obtain a product rich in ethylene and propylene, $C_4$-$C_6$ non-aromatic hydrocarbon mixture and an aqueous phase, wherein a part or all of the aqueous phase is used as the oxygenate feedstock.

According to an embodiment of the invention, the stripper is an independent device. According to an embodiment of the invention, a part of the mixed catalyst and a part of the first particulate catalyst are fed into the same stripper.

It will be understood by those skilled in the art that in the present invention, the stripper primarily functions to remove catalyst-entrained impurities, such as entrained reaction oil and gas. Thus, according to an embodiment of the invention, the stripper can be replaced by any other device capable of performing the primary function, as long as it does not significantly damage the purpose of the invention.

It will be understood by those skilled in the art that in step b), the primary function of the outside heat-exchanger is to cool the mixed catalyst, to fit the needs of the reaction in the fast bed reactor. Thus, according to an embodiment of the invention, the outside heat-exchanger can be replaced by any other device capable of performing the primary function, as long as it does not significantly damage the purpose of the invention. Accordingly, the outside heat-exchanger may be replaced with an internal heat-exchanger.

The present invention does not set any special requirement on the light hydrocarbon feedstock, and a light hydrocarbon feedstock commonly used in the field can be used in the invention, and according to an embodiment of the invention, the light hydrocarbon feedstock is $C_4$-$C_6$ non-aromatic hydrocarbon mixture, and preferably, the light hydrocarbon feedstock at least comprises $C_4$-$C_6$ non-aromatic hydrocarbon mixture obtained from the separation unit.

According to an embodiment of the present invention, for the light hydrocarbon feedstock, a $C_4$-$C_6$ non-aromatic hydrocarbon mixture coming from the separation unit accounts for greater than 20 wt %, and the remaining of the $C_4$-$C_6$ non-aromatic hydrocarbon mixture comes from a catalytic cracking and/or steam cracking unit.

In the present invention, the composition of the $C_4$-$C_6$ non-aromatic hydrocarbon mixture may, for example, contain one or more of isobutene, 1-butene, n-butane, isobutane, isopentene, n-pentene, n-pentane, n-hexene, and isohexene.

In the present invention, the composition of the oxygenate feedstock is not particularly limited, and any mixture commonly used in the art comprising water and an oxygenate may be used in the present invention, and for the present invention, it is preferable that the oxygenate feedstock comprises oxygenate in an amount of 5 to 60 wt %, and water in an amount of 40 to 95 wt %.

In the present invention, the category of the oxygenate is widely selected, and according to an embodiment of the present invention, the oxygenate contains methanol and one or more of ethanol, propanol, butanol, acetaldehyde, propionaldehyde, butyraldehyde, acetone, butanone, formic acid, acetic acid, and propionic acid; preferably, the oxygenate comprise the aldehyde and/or ketone in an amount of 30 to 90 wt %.

According to one variation of the embodiment of the invention, the riser 203 is provided with an oxygenate or light hydrocarbon feed inlet, for reacting with the regenerated catalyst to obtain an additional reaction product comprising ethylene-propylene.

The type of the heat-removing medium 19 is not limited by the present invention, and any medium capable of providing heat, such as water, may be used. For illustration, the heat-removing medium used in Examples is water.

In the present invention, the operation conditions within the fast bed reactor 201 is not specially limited, and any operation conditions generally used in the art can be adopted. According to an embodiment of the present invention, the fast bed reactor 201 is operated at a catalyst temperature of 450 to 500° C., a gas linear velocity of 0.8 to 3 m/s, a reaction gauge pressure of 0.01 to 0.5 MPa, and a catalyst density of 50 to 250 kg/$m^3$.

In the present invention, the mean square error, σ, of the first particulate catalyst fraction is calculated as follows:

$$\sigma^2 = \sum_{i=1}^{n} \left(x_i \sqrt{x} - 1\right)^2 / n$$

$$x_i = (c_c - c_i)/(c_c - c_r)$$

$$\overline{x} = \sum_{i=1}^{n} x_i$$

wherein $C_c$ denotes a percentage content of carbon on the catalyst at the lower branch pipe (38) of the fast bed fast separator based on the total weight of the catalyst; $C_r$ denotes a percentage content of carbon on the first particulate catalyst based on the total weight of the catalyst; and $C_i$ denotes a percentage content of carbon on the catalyst at any point in the fast bed settler (202) based on the total weight of the catalyst.

According to the invention, the purpose of the invention can be achieved by additionally arranging an outside riser reactor and operating according to the process of the invention, without special requirement on the operation conditions in the outside riser reactor 205, and for the invention preferably, in the outside riser reactor 205, the temperature of the catalyst is 530-650° C., the gas linear velocity is 1.1-15 m/s, and the catalyst density is 20-100 kg/$m^3$.

According to a preferred embodiment of the invention, in step b): the weight ratio between the part of the mixed catalyst in the fast bed settler 202 fed into the stripper, the part of the mixed catalyst in the fast bed settler 202 returned to the reaction section of the fast bed reactor 201, and the part of the mixed catalyst in the fast bed settler 202 fed into the outside heat-exchanger is (0.5-1):(5-7):(2-4.5).

According to a preferred embodiment of the invention, in step d): the weight ratio of the part of the first particulate catalyst fed into the stripper to the part of the first particulate catalyst fed into the riser 203 is (1-3):(7-9).

According to an embodiment of the invention, the weight ratio of the light hydrocarbon feedstock to the oxygenate feedstock is 1:(0.5-3). The ethylene-propylene yield can be improved by the preferred embodiment described above.

According to the present invention, preferably, the catalyst is a molecular sieve catalyst.

According to the present invention, preferably, the molecular sieve catalyst is at least one of a SAPO-34 molecular sieve catalyst, a ZSM-5 molecular sieve catalyst and a β molecular sieve catalyst, more preferably a SAPO-34 molecular sieve catalyst. Using the preferred embodiment of the invention, the conversion and the yield of the lower olefin are improved.

According to an embodiment of the invention, the regenerated catalyst has a carbon content of less than 0.1% by weight, based on the total weight of the catalyst.

According to an embodiment of the invention, the first lifting medium is not specially limited and may be, for example, steam and/or the oxygenate feedstock and/or the light hydrocarbon feedstock.

According to an embodiment of the invention, the second lifting medium is not specially limited and may be, for example, the methanol feedstock from the process for producing ethylene-propylene.

The invention mainly modifies the structure and the operation procedures of the reaction system, and the rest operation conditions, processes and steps which are not particularly described can adopt the conventional processes, conditions and steps.

In the invention, the total yield of the ethylene and propylene, calculated as carbon, is calculated by: (the total yield of the ethylene and propylene, calculated as carbon,) =(the weight of the ethylene and the propylene)/(the weight of the methanol feed, calculated as carbon,)×100%.

(the weight of the methanol feed, calculated as carbon,)=(the weight of the methanol feed)*14/32.

Thus, the present invention provides a number of embodiments of a first exemplary series, including:

1. A mixing device for mixing at least two particulate catalysts, comprising a riser 103 for loading a first particulate catalyst and an outer casing vessel 101 surrounding and being coaxial with the riser for loading a second particulate catalyst, the first and second particulate catalysts being different in structure and/or composition, and at least a part of the upper portion of the riser 103 and at least a part of the upper portion of the outer casing vessel 101 both being located inside a mixing zone vessel 102; wherein:
   - the bottom of the riser 103 is provided with a riser feed inlet for a first lifting medium 110, which is used for delivering upwards the first particulate catalyst loaded in the riser 103; the top of the riser 103 has a riser outlet structural member 108 for allowing the upward-delivered first particulate catalyst to be fed into the interior of the mixing zone vessel 102 via the riser outlet structural member 108;
   - the bottom of the outer casing vessel 101 is provided with a second lifting medium feed inlet 109, which is used for delivering upwards the second particulate catalyst loaded in the outer casing vessel 101; the top of the outer casing vessel 101 is provided with an outer casing vessel outlet structural member 107 which is used for allowing the second particulate catalyst delivered upwards to be fed into the interior of the mixing zone vessel 102 through the outer casing vessel outlet structural member 107 and be mixed with the first particulate catalyst to obtain a mixed catalyst.

2. The mixing device according to embodiment 1 of the first exemplary series, wherein the first and second particulate catalysts are distributed such that the Peclet number of the mixed catalyst is less than 5, and the mean square error, σ, of the first particulate catalyst fraction is less than 3.0; or the Peclet number of the mixed catalyst is less than 1, and the mean square error, σ, of the first particulate catalyst fraction is less than 1.0.

3. The mixing device according to embodiment 1 of the first exemplary series, wherein the interior of the mixing zone vessel 202 is provided with an annular distributor surrounding and being coaxial with the upper portion of the outer casing vessel 201 for delivering a fluidizing gas (e.g., steam) upward into the interior of the mixing zone vessel 202 to act on the first and second particulate catalysts.

6. The mixing device according to embodiment 1 of the first exemplary series, wherein the ratio by weight of the flow rates entering the mixing zone vessel, Rw, of the first particulate catalyst to the second particulate catalyst is 0.01<Rw≤0.5, preferably 0.02<Rw≤0.2.

7. The mixing device according to embodiment 1 of the first exemplary series, wherein the outer casing vessel outlet structural member 107 is of a branch pipe structure; and/or the riser outlet structural member 108 is of a branch pipe structure or a flow guiding structure.

8. The mixing device according to embodiment 1 of the first exemplary series, wherein the upper portion of the riser 103 extends beyond the top of the outer casing vessel 101, so that the riser outlet structural member 108 is located above the outer casing vessel outlet structural member 107.

9. The mixing device according to embodiment 1 of the first exemplary series, wherein the riser outlet structural member 108 is located inside the outer casing vessel outlet structural member 107, such that the first particulate catalyst is premixed with the second particulate catalyst inside the outer casing vessel outlet structural member 107.

10. The mixing device according to embodiment 1 of the first exemplary series, which is used in a reaction system for producing ethylene-propylene, wherein:

- the outer casing vessel 101 is a fast bed reactor 201, allowing that contact and reaction of the feedstocks with the catalyst to produce ethylene-propylene is mainly carried out therein, and the second particulate catalyst is obtained from partial deactivation in the reaction;
- the first particulate catalyst is a regenerated catalyst obtained by a regeneration treatment and optionally other treatments.

11. The mixing device according to embodiment 10 of the first exemplary series, wherein the riser 103 is further provided with an oxygenate or light hydrocarbon feed inlet, for reaction with the regenerated first particle to obtain an additional reaction product comprising ethylene-propylene.

12. The mixing device according to embodiment 10 of the first exemplary series, wherein the riser 103 is externally provided with a heat-exchanging coiler or jacket, for removing or supplementing heat from/to the riser 103 and/or outer casing vessel 101.

13. A mixing device for mixing at least two particulate catalysts, having a first catalyst feeding equipment for loading a first particulate catalyst and a second catalyst feeding equipment for loading a second particulate catalyst, and a mixing zone vessel located above the first and second catalyst feeding equipment into which the first and second particulate catalysts are fed to mix to obtain a mixed catalyst; wherein:

- within the mixing zone vessel, the first and second particulate catalysts are distributed such that the Peclet number of the mixed catalyst is less than 5, and the mean square error, σ, of the first particulate catalyst fraction is less than 3.0; or the Peclet number of the mixed catalyst is less than 1, and the mean square error, σ, of the first particulate catalyst fraction is less than 1.0; and wherein
- the ratio by weight of the flow rates entering the mixing zone vessel, Rw, of the first particulate catalyst to the second particulate catalyst is $0.01<Rw\leq0.5$, preferably $0.02<Rw\leq0.2$.

14. A reaction system for producing ethylene-propylene, comprising: a fast bed reactor 201, a fast bed settler 202 and a riser 203 which are coaxially arranged; wherein

- the riser 203 is located, in the radial direction, within the fast bed reactor 201; the bottom of the riser 203 is provided with a riser feed inlet 210 for a first lifting medium; the top outlet of the riser 203 is connected with a riser outlet structural member 208 through which the regenerated first particulate catalyst obtained by a regeneration treatment and optional other treatment is delivered into the fast bed settler 202;
- the fast bed reactor 201 is used for allowing that contact and reaction of the feedstocks with the catalyst to produce ethylene-propylene is mainly carried out therein, during which reaction the catalyst is at least partially deactivated; the top of the fast bed reactor 201 is connected with a fast bed outlet structural member 207, a second particulate catalyst obtained from the partial deactivation is delivered into the fast bed settler 202 and is mixed with the regenerated first particulate catalyst to obtain a mixed catalyst;
- the riser outlet structural member 208 and the fast bed outlet structural member 207 are both located within the fast bed settler 202, and the riser outlet structural member 208 is located above the fast bed outlet structural member 207;
- wherein the riser outlet structural member 208 and the fast bed outlet structural member 207 are each preferably a fast separator.

15. A mixing device for mixing at least two particulate materials, comprising a riser for loading a first particle and an outer casing vessel surrounding and being coaxial with the riser for loading a second particle, the upper portion of the first riser extending beyond the top of the second riser, and at least a part of the upper portion of the first riser and at least a part of the second riser both being located inside a mixing zone vessel, such that the first and second particles are delivered through the first and second risers, respectively, to the interior of the mixing zone vessel and mixed.

In addition, the present invention provides a number of embodiments of a second exemplary series, including:

1. A reaction system for producing ethylene-propylene, comprising: a fast bed reactor 201, a second dense bed I, a riser, outside heat-exchanger, a riser reactor, a second dense bed II, a stripper and a regenerator; wherein:

- the riser pipe is coaxial with the fast bed reactor and the second dense bed I, and the riser pipe is located inside the fast bed reactor;
- the riser outlet is connected with the riser fast separator or the riser outlet structural member, and the top of the fast bed reactor is connected with a fast bed fast separator;
- the riser fast separator and the fast bed fast separator are both located within the second dense bed, and the riser fast separator is located above the fast bed fast separator;
- the riser outlet structural member is located inside the fast bed fast separator;
- the riser reactor and the second dense bed II are coaxial, and the middle-upper part and the outlet of the riser reactor are located inside the second dense bed II;
- wherein, the spent catalyst outlet of the second dense bed II is communicated with the feed inlet of the riser and is communicated with the feed inlet of the stripper, the spent catalyst outlet of the second dense bed I is communicated with the feed inlet of the stripper and is communicated with the feed inlet of the outside heat-exchanger, the solid outlet of the stripper is communicated with the solid feed inlet of the second dense bed, and the outlet of the heat-removed product of the outside heat-exchanger is communicated with the upper opening of the second dense bed.

2. The reaction system according to embodiment 1 of the second exemplary series, wherein,

- the riser fast separator consists of riser fast separator lower branch pipes and riser fast separator horizontal pipes, wherein the riser fast separator horizontal pipes are horizontally arranged, and the included angle between the riser fast separator lower branch pipe and the riser fast separator horizontal pipe is 90 degrees;

the riser fast separator lower branch pipes of the riser fast separator are uniformly distributed; and/or the number, n, of riser fast separator lower branch pipes of the riser fast separator is 2-8; and the included angle, β, between adjacent riser fast separator lower branch pipes equals to 45-180 degrees; and/or the fast bed fast separator consists of fast bed fast separator lower branch pipes and fast bed fast separator horizontal pipes, wherein the fast bed fast separator horizontal pipes are horizontally arranged, and the included angle between the fast bed fast separator lower branch pipe and the fast bed fast separator horizontal pipe is 90 degrees;

the fast bed fast separator lower branch pipes of the fast bed fast separator are uniformly distributed; and/or the number, m, of fast bed fast separator lower branch pipes of the fast bed fast separator is 2-8; and the included angle, α, between adjacent fast bed fast separator lower branch pipes equals to 45-180 degrees; and/or the riser fast separator lower branch pipes and the fast bed fast separator lower branch pipes are distributed crosswise.

3. The reaction system according to embodiment 1 or 2 of the second exemplary series, wherein the ratio between the distance from the center point of the fast bed fast separator to the center point of the fast bed fast separator lower branch pipe and the distance from the center point of the riser fast separator to the riser fast separator lower branch pipe is (0.3-1):1.

4. The reaction system according to any one of embodiments 1-3 of the second exemplary series, wherein the riser outlet structural member is composed of a diffusion cone and a diffusion plate, the riser outlet is connected to the diffusion cone, and the diffusion cone is connected to the diffusion plate; the distance between the riser outlet and the top of the fast bed fast separator lower branch pipe is h1, the distance from the connection point of the diffusion cone and the diffusion plate to the top of the fast bed fast separator lower branch pipe is h3, the distance between the edge point of the diffusion plate and the top of the fast bed fast separator lower branch pipe is h2, and the distance between the top of the fast bed fast separator and the top of the fast bed fast separator lower branch pipe is H; the included angle between the diffusion cone and the vertical direction is γ, and the included angle between the diffusion plate and the horizontal direction is δ; the ratio of h1 to H is (0.05-0.3):1, the ratio of h2 to H is (0.2-0.5):1, and the ratio of h3 to H is (0.4-0.6):1; h3 is greater than h2; γ is 10-60 degrees, and δ is 30-80 degrees.

5. A process for producing ethylene-propylene, the process being carried out in a reaction system according to any one of embodiments 1 to 4 of the second exemplary series, the process comprising:

a) feeding a methanol feedstock into a fast bed reactor to be contacted and reacted with a catalyst to obtain a reaction product I, and delivering upward the coked catalyst into a second dense bed I through the fast bed fast separator;

b) feeding a part of the spent catalyst from the second dense bed I into a stripper, and returning a part of the spent catalyst I to the fast bed reactor, and feeding another part of the spent catalyst into an outside heat-exchanger to be contacted with a heat-removing medium for cooling followed by being returned to the fast bed reactor;

c) feeding a light hydrocarbon feedstock and a feedstock mixture into the outside riser reactor to be contacted with the catalyst, for reaction during the upward delivering thereof, and being fed into the second dense bed II, to obtain a reaction product II and a spent catalyst II, wherein the feedstock mixture contains water and an oxygenate;

d) feeding a part of the spent catalyst II from the second dense bed II into the stripper, and another part of the spent catalyst II into the riser; wherein the spent catalyst II fed into the riser enters the second dense bed I through the riser fast separator by the lifting of a riser lifting medium;

e) feeding the catalyst from the stripper, after being stripped by a stripping medium, into a regenerator to be contacted with a regenerating medium to burn coke on the catalyst to obtain a regenerated catalyst and flue gas;

f) degassing the regenerated catalyst and then feeding the degassed regenerated catalyst into the riser reactor; and feeding the reaction product I and the reaction product II together into a separation unit to obtain a product rich in ethylene and propylene, $C_4$-$C_6$ non-aromatic hydrocarbon mixture and an aqueous phase, wherein a part or all of the aqueous phase is used as the feedstock mixture.

6. The process according to embodiment 5 of the second exemplary series, wherein, the light hydrocarbon feedstock is a $C_4$-$C_6$ non-aromatic hydrocarbon mixture, and preferably, the light hydrocarbon feedstock at least comprises a $C_4$-$C_6$ non-aromatic hydrocarbon mixture obtained from the separation unit;

more preferably, for the light hydrocarbon feedstock, a $C_4$-$C_6$ non-aromatic hydrocarbon mixture coming from the separation unit accounts for greater than 20 wt %, and the remaining of the $C_4$-$C_6$ non-aromatic hydrocarbon mixture comes from a catalytic cracking and/or steam cracking unit;

preferably, the $C_4$-$C_6$ non-aromatic hydrocarbon mixture comprises one or more of isobutene, 1-butene, n-butane, isobutane, isopentene, n-pentene, n-pentane, n-hexene, and isohexene.

the feedstock mixture comprises oxygenate in an amount of 5-60 wt % and water in an amount of 40-95 wt %; wherein the oxygenate contains methanol and one or more of ethanol, propanol, butanol, acetaldehyde, propionaldehyde, butyraldehyde, acetone, butanone, formic acid, acetic acid, and propionic acid; preferably, the oxygenate comprise the aldehyde and/or ketone in an amount of 30-90 wt %.

7. The process according to embodiment 5 or 6 of the second exemplary series, wherein, the fast bed reactor is operated at a catalyst temperature of 450 to 500° C., a gas linear velocity of 0.8 to 3 m/s, a reaction gauge pressure of 0.01 to 0.5 MPa, and a catalyst density of 50 to 250 kg/$m^3$; and/or the riser reactor is operated at a temperature of the catalyst of 530-650° C., a gas linear velocity of 1.1-15 m/s, and a catalyst density of 20-100 kg/$m^3$; and/or in step b): the weight ratio between the part of the spent catalyst in the second dense bed I fed into the stripper, the part of the spent catalyst in the second dense bed I returned to the fast bed reactor, and the part of spent catalyst in the second dense bed I fed into the outside heat-exchanger is (0.5-1):(5-7):(2-4.5);

in step d): the weight ratio of the part of the spent catalyst II fed into the stripper to the part of the spent catalyst II fed into the riser 203 is (1-3):(7-9).

8. The process according to any one of the embodiments 5-7 of the second exemplary series, wherein the weight ratio of the light hydrocarbon feedstock to the feedstock mixture is 1:(0.5-3).

9. The process according to any one of embodiments 5-8 of the second exemplary series, wherein, the catalyst is SAPO-34 molecular sieve catalyst; and/or the regenerated catalyst has a carbon content of less than 0.1% by weight, based on the total weight of the catalyst.

10. The process according to any one of embodiments 5-9 of the second exemplary series, wherein the riser lifting medium is steam and/or feedstock mixture and/or light hydrocarbon feedstock.

Example

The invention is further illustrated by, but is not limited to, the following Examples. In the Examples, reference is primarily made to the embodiment of the mixing device of the present invention for use in an ethylene-propylene reaction system as illustrated in FIG. 9; wherein the riser outlet structural member, fast bed outlet structural member, etc. are described with reference to the embodiments shown in FIG. 3-7.

Example 1

The device shown in FIG. 9 was used.

Referring to FIG. 4, the number, n, of the riser fast separator lower branch pipes 39 of the riser fast separator 208 was 2; and the included angle, β, between adjacent riser fast separator lower branch pipes 39 equaled to 180 degrees: the number, m, of the fast bed fast separator lower branch pipes 38 of the fast bed fast separator 207 was 2; and the included angle, α, between adjacent fast bed fast separator lower branch pipes 38 equaled to 180 degrees; and the riser fast separator lower branch pipe 39 and the fast bed fast separator lower branch pipe 38 were distributed crosswise.

The ratio between the distance from the center point of the fast bed fast separator 207 to the center point of the fast bed fast separator lower branch pipe 38 and the distance from the center point of the riser fast separator 208 to the riser fast separator lower branch pipe 39 was 0.8:1.

The process comprised:

a) feeding a methanol feedstock into the fast bed reactor 201 through the methanol feed inlet 209 to be contacted and reacted with a catalyst to obtain a reaction product I, from which a second particulate catalyst obtained from partial deactivation was delivered upward and was fed into a fast bed settler 202 through a fast bed fast separator 207;

b) feeding a part of the mixed catalyst (stream 9) from the fast bed settler 202 into a stripper 7, and returning a part of the mixed catalyst (stream 9) to the fast bed reactor 201, and feeding another part of the mixed catalyst (stream 9) into an outside heat-exchanger 4 to be contacted with a heat-removing medium 19 for cooling followed by being returned to the fast bed reactor 201;

c) feeding a light hydrocarbon feedstock and an oxygenate feedstock into the outside riser reactor 205 to be contacted with the regenerated catalyst, for reaction during the upward delivering thereof, and being fed into the riser settler 206, to obtain a reaction product II and a first particulate catalyst, wherein the oxygenate feedstock contained water and an oxygenate;

d) feeding a part of the first particulate catalyst (stream 10) from the riser settler 206 into a stripper 7, and another part of the first particulate catalyst (stream 10) into the riser 203; wherein the first particulate catalyst fed into the riser 203 entered the fast bed settler 202 through the riser fast separator 208 by the lifting of a first lifting medium;

e) feeding the catalyst from the stripper, after being stripped by a stripping medium 24, into a regenerator to be contacted with a regenerating medium 26 to burn coke on the catalyst to obtain a regenerated catalyst 27 and flue gas 25;

f) degassing the regenerated catalyst 27 and then feeding the degassed regenerated catalyst into the outer riser reactor 205; and feeding the reaction product I and the reaction product II together, through a product outlet 212, into a separation unit to obtain a product rich in ethylene and propylene, $C_4$-$C_6$ non-aromatic hydrocarbon mixture and an aqueous phase, wherein a part or all of the aqueous phase was used as the oxygenate feedstock.

In step b): the weight ratio between the part of the mixed catalyst in the fast bed settler 202 fed into the stripper, the part of the mixed catalyst in the fast bed settler 202 returned to the fast bed reactor 201, and the part of the mixed catalyst in the fast bed settler 202 fed into the outside heat-exchanger was 0.8:6:3.2.

In step d): the weight ratio between the part of the first particulate catalyst fed into the stripper and the part of the first particulate catalyst fed into the riser 203 was 2:8.

The light hydrocarbon feedstock was $C_4$-$C_6$ non-aromatic hydrocarbon mixture obtained by the separation unit, comprising butylene in an amount of 60 wt %, pentene in an amount of 30 wt %, hexylene in an amount of 10 wt %; the oxygenate feedstock comprised oxides in a total amount of 50 wt %, wherein, the oxides comprised, by weight, methanol in an amount of 19%, ethanol in an amount of 5%, propanol in an amount of 3%, butanol in an amount of 2%, acetaldehyde in an amount of 8%, propionaldehyde in an amount of 2%, acetone in an amount of 40%, butanone in an amount of 20%, and formate in an amount of 1%.

The fast bed reactor 201 was operated at a catalyst temperature of 490° C., a gas linear velocity of 2 m/s, a reaction gauge pressure of 0.2 MPa, and a catalyst density of 70 kg/$m^3$; and the outside riser reactor 205 was operated at a temperature of the catalyst of 600° C., a gas linear velocity of 5 m/s, and a catalyst density of 40 kg/$m^3$.

The weight ratio of the light hydrocarbon feedstock to the oxygenate feedstock was 1:1.

The catalyst was SAPO-34 molecular sieve catalyst; and the regenerated catalyst 27 had a carbon content of 0.05% based on the total weight of the catalyst.

The first lifting medium was steam.

In the Example, the total yield, calculated as carbon, of ethylene and propylene was 90.4 wt %.

Example 2

According to the process of Example 1, the device shown in FIG. 9 was used, except that the structure of the riser fast separator 208 shown in FIG. 4 was replaced with the structure of the riser outlet 208 shown in FIG. 6.

Among others, the ratio of h1 to H was 0.05:1, the ratio of h2 to H was 0.2:1, and the ratio of h3 to H was 0.4:1; γ was 60 degrees, and δ was 30 degrees.

The light hydrocarbon feedstock comprised butylene in an amount of 30 wt %, butane in an amount of 20 wt %, pentene in an amount of 45 wt %, hexylene in an amount of 5 wt %; and the oxygenate feedstock comprised oxides in a total amount of 60 wt %, wherein the oxides comprised, by weight, methanol in an amount of 5%, ethanol in an amount of 3%, propanol in an amount of 2%, acetaldehyde 20%, acetone in an amount of 50%, and butanone in an amount of 20%.

The fast bed reactor 201 was operated at a catalyst temperature of 490° C., a gas linear velocity of 2 m/s, a reaction gauge pressure of 0.2 MPa, and a catalyst density of 70 kg/$m^3$; and the outside riser reactor 205 was operated at a temperature of the catalyst of 600° C., a gas linear velocity of 5 m/s, and a catalyst density of 40 kg/$m^3$.

The weight ratio of the light hydrocarbon feedstock to the oxygenate feedstock was 1:1.

The catalyst was SAPO-34 molecular sieve catalyst; and the regenerated catalyst 27 had a carbon content of 0.05% based on the total weight of the catalyst.

The first lifting medium was steam.

In the Example, the total yield, calculated as carbon, of ethylene and propylene was 89.3 wt %.

Example 3

Lower olefins were produced according to the system and process of Example 2, except that δ was 80°, γ was 10°, the ratio of $h_1$ to H was 0.3:1, the ratio of $h_2$ to H was 0.5:1, and the ratio of $h_3$ to H was 0.6:1; while the rest was the same as in Example 2.

In the Example, the total yield, calculated as carbon, of ethylene and propylene was 90.1 wt %.

Example 4

Lower olefins were produced according to the system and process of Example 2, except that δ was 90°, γ was 70°, the ratio of $h_1$ to H was 0.4:1, the ratio of $h_2$ to H was 0.1:1, and the ratio of $h_3$ to H was 0.3:1; while the rest was the same as in Example 2.

In the Example, the total yield, calculated as carbon, of ethylene and propylene was 86.3 wt %.

Example 5

Lower olefins were produced according to the system and process of Example 1, except that the number, n, of the riser fast separator lower branch pipes 39 of the riser fast separator 208 was 8; and the included angle, β, between adjacent riser fast separator lower branch pipes 39 equaled to 45 degrees; the number, m, of the fast bed fast separator lower branch pipes 38 of the fast bed fast separator 207 was 8, and the included angle, α, between adjacent fast bed fast separator lower branch pipes 38 equaled to 45 degrees; and the riser fast separator lower branch pipe 39 and the fast bed fast separator lower branch pipe 38 were distributed crosswise.

The ratio between the distance from the center point of the fast bed fast separator 207 to the center point of the fast bed fast separator lower branch pipe 38 and the distance from the center point of the riser fast separator 208 to the riser fast separator lower branch pipe 39 was 1:1.

In the Example, the total yield, calculated as carbon, of ethylene and propylene was 90.2 wt %.

Example 6

Lower olefins were produced according to the system and process of Example 1, except that the number, n, of the riser fast separator lower branch pipes 39 of the riser fast separator 208 was 10; and the included angle, β, between adjacent riser fast separator lower branch pipes 39 equaled to 18 degrees; the number, m, of the fast bed fast separator lower branch pipes 38 of the fast bed fast separator 207 was 10; and the included angle, α, between adjacent fast bed fast separator lower branch pipes 38 equaled to 18 degrees; and the riser fast separator lower branch pipe 39 and the fast bed fast separator lower branch pipe 38 were distributed crosswise.

The ratio between the distance from the center point of the fast bed fast separator 207 to the center point of the fast bed fast separator lower branch pipe 38 and the distance from the center point of the riser fast separator 208 to the riser fast separator lower branch pipe 39 was 1.5:1.

In the Example, the total yield, calculated as carbon, of ethylene and propylene was 88.7 wt %.

Example 7

Lower olefins were produced according to the system and process of Example 1, except that the fast bed reactor 201 was operated at a catalyst temperature of 450° C., a gas linear velocity of 0.8 m/s, a reaction gauge pressure of 0.01 MPa, and a catalyst density of 250 kg/$m^3$; and the outside riser reactor 205 was operated at a temperature of the catalyst of 530° C., a gas linear velocity of 1.1 m/s, and a catalyst density of 100 kg/$m^3$.

In the Example, the total yield, calculated as carbon, of ethylene and propylene was 87.6 wt %.

Example 8

Lower olefins were produced according to the system and process of Example 1, except that the fast bed reactor 201 was operated at a catalyst temperature of 500° C., a gas linear velocity of 3 m/s, a reaction gauge pressure of 0.5 MPa, and a catalyst density of 50 kg/$m^3$; and the outside riser reactor 205 was operated at a temperature of the catalyst of 650° C., a gas linear velocity of 15 m/s, and a catalyst density of 20 kg/$m^3$.

In the Example, the total yield, calculated as carbon, of ethylene and propylene was 89.1 wt %.

Example 9

Lower olefins were produced according to the system and process of Example 1, except that the number, n, of the riser fast separator lower branch pipes 39 of the riser fast separator 208 was 1; the number, m, of the fast bed fast separator lower branch pipes 38 of the fast bed fast separator 207 was 1; and the fast bed fast separator lower branch pipe 38 and the riser fast separator lower branch pipe 39 were aligned in line.

In the Example, the total yield, calculated as carbon, of ethylene and propylene was only 84.1 wt %.

Comparative Example 1

Example 1 was repeated, except that the outside riser reactor 205 and riser settler 206 were absent, and the regenerated catalyst 27 was fed directly into the fast bed reactor 201 to participate in the reaction.

In the Example, the total yield, calculated as carbon, of ethylene and propylene was only 82.4 wt %.

Comparative Example 2

Lower olefins were produced according to the system and process of Example 1, except that the riser 203 and the fast separator configuration were absent, while the first particulate catalyst (stream 10) was fed directly into the fast bed reactor 201.

In the Example, the total yield, calculated as carbon, of ethylene and propylene was 85.2 wt %.

Comparative Example 3

Example 2 was repeated, except that the outlet of the outside riser reactor 3 was connected directly with the fast bed settler 202.

In the Example, the total yield, calculated as carbon, of ethylene and propylene was only 83.3 wt %.

The preferred embodiments of the present invention have been described in detail above with reference to the accompanying drawings, but the present invention is not limited thereto.

Within the scope of the technical idea of the invention, numerous simple variants are possible, comprising the combination of the individual specific technical features in any suitable manner. The various potential combination manners of the present invention are not described in detail in order to avoid unnecessary repetition. Such simple modifications and combinations should also be considered as disclosed in the present invention, and all such modifications and combinations are intended to be included within the scope of the present invention.

The invention claimed is:

1. A mixing device for mixing at least two particulate catalysts, comprising a riser for loading a first particulate catalyst and an outer casing vessel coaxially disposed about the riser for loading a second particulate catalyst, the first and second particulate catalysts being different in structure and/or composition, and at least a part of the upper portion of the riser and at least a part of the upper portion of the outer casing vessel both being located inside a mixing zone vessel;

wherein:

the bottom of the riser is provided with a riser feed inlet of a first lifting medium for delivering upwards the first particulate catalyst loaded in the riser; the top of the riser has a riser outlet structural member configured to introduce the upward-delivered first particulate catalyst into the interior of the mixing zone vessel via the riser outlet structural member; and the bottom of the outer casing vessel is provided with a feed inlet of a second lifting medium for delivering upwards the second particulate catalyst loaded in the outer casing vessel; the top of the outer casing vessel has an outer casing vessel outlet structural member configured to introduce the upward-delivered second particulate catalyst into the interior of the mixing zone vessel via the outer casing vessel outlet structural member, and to be mixed with the first particulate catalyst to form a mixed catalyst.

2. The mixing device according to claim 1, wherein the first and second particulate catalysts are distributed such that a Peclet number of the mixed catalyst is less than 5, and a mean square error, σ, of the first particulate catalyst fraction is less than 3.0; or the Peclet number of the mixed catalyst is less than 1, and the mean square error, σ, of the first particulate catalyst fraction is less than 1.0.

3. The mixing device according to claim 1, wherein the interior of the mixing zone vessel is provided with an annular distributor coaxially disposed about the upper portion of the outer casing vessel for delivering upward a fluidizing gas into the interior of the mixing zone vessel to contact the first and second particulate catalysts.

4. The mixing device according to claim 1, wherein a ratio by weight of the flow rates entering the mixing zone vessel, Rw, of the first particulate catalyst to the second particulate catalyst is $0.01<Rw\leq0.5$.

5. The mixing device according to claim 1, wherein the outer casing vessel outlet structural member is of a branch pipe structure; and/or the riser outlet structural member is of a branch pipe structure or a flow guiding structure.

6. The mixing device according to claim 1, wherein the upper portion of the riser extends beyond the top of the outer casing vessel, so that the riser outlet structural member is located above the outer casing vessel outlet structural member.

7. The mixing device according to claim 1, wherein the riser outlet structural member is located inside the outer casing vessel outlet structural member such that the first particulate catalyst is premixed with the second particulate catalyst inside the outer casing vessel outlet structural member.

8. The mixing device according to claim 1, which is configured to be used in a reaction system for producing ethylene-propylene, wherein:

the outer casing vessel is a fast bed reactor configured to feedstocks and a catalyst to react to produce ethylene-propylene therein, and the catalyst is the second particulate catalyst obtained from partial deactivation in the reaction; and the first particulate catalyst is a regenerated catalyst obtained by a regeneration treatment.

9. The mixing device according to claim 8, wherein the riser is further provided with an oxygenate or light hydrocarbon feed inlet, the riser is configured to allow reaction between an oxygenate or a light hydrocarbon feed in the presence of the regenerated first particle to obtain a reaction product comprising ethylene-propylene.

10. The mixing device according to claim 1, wherein the riser is externally provided with a heat-exchanging coiler or jacket, for removing or supplementing heat from/to the riser and/or outer casing vessel.

11. A mixing device for mixing at least two particulate catalysts, having a first catalyst feeding equipment for loading a first particulate catalyst and a second catalyst feeding equipment for loading a second particulate catalyst, and a mixing zone vessel located above the first and second catalyst feeding equipment into which the first and second particulate catalysts are fed to mix to obtain a mixed catalyst, wherein:

within the mixing zone vessel, the first and second particulate catalysts are distributed such that a Peclet number of the mixed catalyst is less than 5, and mean square error, σ, of the first particulate catalyst fraction is less than 3.0; or the Peclet number of the mixed catalyst is less than 1, and the mean square error, σ, of the first particulate catalyst fraction is less than 1.0; and a ratio by weight of the flow rates entering the mixing zone vessel, Rw, of the first particulate catalyst to the second particulate catalyst is $0.01<Rw\leq0.5$.

12. A mixing device for mixing at least two particulate materials, comprising a first riser for loading a first particle and a second riser surrounding and being coaxial with the first riser for loading a second particle, the upper portion of the first riser extending beyond the top of the second riser, and at least a part of the upper portion of the first riser and at least a part of the second riser both being located inside a mixing zone vessel, such that the first and second particles are delivered through the first and second risers, respectively, to the interior of the mixing zone vessel and mixed.

* * * * *